United States Patent
Bowen et al.

(10) Patent No.: US 10,059,514 B2
(45) Date of Patent: Aug. 28, 2018

(54) METHOD OF DISPOSING OF SOILED MATERIALS IN A LINED STORAGE BIN

(71) Applicant: Synaptic Wireless, LLC, O'Fallon, MO (US)

(72) Inventors: Charles H. Bowen, O'Fallon, MO (US); P. Mark Bowen, Fayetteville, GA (US)

(73) Assignee: Synaptic Wireless, LLC, O'Fallon, MO (US)

( * ) Notice: Subject to any disclaimer, the term of this patent is extended or adjusted under 35 U.S.C. 154(b) by 0 days.

(21) Appl. No.: 15/454,815

(22) Filed: Mar. 9, 2017

(65) Prior Publication Data

US 2017/0174426 A1    Jun. 22, 2017

Related U.S. Application Data

(63) Continuation of application No. 13/796,868, filed on Mar. 12, 2013, now Pat. No. 9,617,072.

(51) Int. Cl.
| | |
|---|---|
| *B65F 1/06* | (2006.01) |
| *A61B 50/36* | (2016.01) |
| *A61B 50/30* | (2016.01) |
| *B65F 1/14* | (2006.01) |

(52) U.S. Cl.
CPC ............ *B65F 1/062* (2013.01); *A61B 50/36* (2016.02); *B65F 1/14* (2013.01); *A61B 2050/314* (2016.02); *B65F 2210/181* (2013.01); *B65F 2240/00* (2013.09)

(58) Field of Classification Search
CPC .......... B65F 1/062; B65F 1/14; B65F 1/1405; B65F 1/16; B65F 1/1607; B65F 2210/181; B65F 2240/145; A61B 50/36; A61B 50/37; A61B 2050/375

USPC ........ 53/449, 459, 469, 473, 480–483, 175, 53/570, 567, 576, 577; 220/495.01, 220/495.04, 495.05, 495.06, 495.07, 220/495.08, 495.11, 908.1, 908.3

See application file for complete search history.

(56) References Cited

U.S. PATENT DOCUMENTS

| | | | |
|---|---|---|---|
| 1,984,170 A | 12/1934 | Archbold, Jr. | |
| 2,352,503 A * | 6/1944 | Walton | B65D 5/5059 53/175 |
| 2,720,346 A | 10/1955 | Compton | |
| 2,903,154 A | 9/1959 | Hendershot | |
| 3,133,668 A * | 5/1964 | Heise | B44D 3/128 220/701 |
| 3,329,307 A | 7/1967 | Jacobson | |
| 3,454,182 A | 7/1969 | Morton | |

(Continued)

FOREIGN PATENT DOCUMENTS

| | | | |
|---|---|---|---|
| FR | 2231582 A1 * | 12/1974 | .............. B65F 1/06 |
| FR | 2967663 A1 * | 5/2012 | ............. B65F 1/067 |
| WO | 2005115881 A1 | 12/2005 | |

OTHER PUBLICATIONS

International Search Report, International Patent Application No. PCT/US2014/015358, dated May 28, 2014 (10 pages).

*Primary Examiner* — Stephen F Gerrity
(74) *Attorney, Agent, or Firm* — Lewis Rice LLC (57) ABSTRACT

Methods and apparatus for maintaining a sanitary disposal and storage bin for consumed medical products using a storage bin with a liner bag and an attached shielding grommet in the shape of a circle flattened on one end which, when soiled, may itself be placed in the liner bag within the container.

3 Claims, 7 Drawing Sheets

(56) References Cited

U.S. PATENT DOCUMENTS

| | | |
|---|---|---|
| 3,722,561 A | 3/1973 | O'Leary et al. |
| 4,009,802 A | 3/1977 | Hayduchok |
| 4,466,553 A | 8/1984 | Zenger |
| D283,492 S | 4/1986 | Nitsch |
| D286,268 S | 10/1986 | Wolff |
| 4,765,579 A | 8/1988 | Robbins, III et al. |
| D305,820 S * | 1/1990 | Beato .......................... D32/54 |
| 4,892,224 A | 1/1990 | Graham |
| 5,065,886 A * | 11/1991 | Sher .......................... B65F 1/14 220/908 |
| 5,065,891 A | 11/1991 | Casey |
| D322,221 S | 12/1991 | Neff |
| 5,143,242 A | 9/1992 | Millasich |
| 5,160,062 A | 11/1992 | Strawder |
| 5,195,662 A | 3/1993 | Neff |
| 5,269,435 A | 12/1993 | Hallock, III |
| 5,299,708 A | 4/1994 | Hallock, III |
| 5,320,241 A | 6/1994 | Evans |
| 5,322,179 A | 6/1994 | Ting |
| 5,385,251 A | 1/1995 | Dunn |
| 5,403,634 A | 4/1995 | Mauffette |
| 5,423,448 A * | 6/1995 | Pedigo ...................... B65F 1/16 220/908 |
| 5,503,292 A | 4/1996 | Cuccharia |
| 5,505,334 A | 4/1996 | Triglia |
| D377,554 S | 1/1997 | Adriaansen |
| 5,615,809 A | 4/1997 | Feer et al. |
| 5,628,424 A | 5/1997 | Gola |
| 5,634,566 A | 6/1997 | Jansen et al. |
| 5,779,093 A | 7/1998 | Poole et al. |
| D432,421 S | 10/2000 | Sullivan, Jr. |
| 6,199,718 B1 | 3/2001 | Ellis |
| 6,213,338 B1 | 4/2001 | Cogdill |
| 6,378,721 B1 | 4/2002 | Williams |
| D457,700 S | 5/2002 | Acord |
| D489,261 S | 5/2004 | Doelling |
| D494,470 S | 8/2004 | Guyot |
| 6,824,005 B1 | 11/2004 | Ashinhurst |
| D509,427 S | 9/2005 | Townsend |
| RE39,726 E | 7/2007 | Lin |
| 7,364,049 B2 | 4/2008 | Panek, Jr. |
| D664,320 S | 7/2012 | Sakko |
| 8,317,055 B2 | 11/2012 | Zawrotny et al. |
| 8,740,012 B2 | 6/2014 | Ekkert |
| 8,752,706 B2 | 6/2014 | Dermo |
| 9,617,072 B2 * | 4/2017 | Bowen et al. ............. B65F 1/06 |
| 2005/0056649 A1 | 3/2005 | Simonson |
| 2006/0283863 A1 | 12/2006 | Coles |
| 2007/0084866 A1 | 4/2007 | Saeugling |
| 2008/0006558 A1 * | 1/2008 | Thrapp .................. B65F 1/1607 206/496 |
| 2008/0264948 A1 | 10/2008 | Kovacevich et al. |
| 2009/0107998 A1 * | 4/2009 | Meissen ................... B65F 1/06 220/254.3 |
| 2010/0219192 A1 * | 9/2010 | Quan ...................... B65F 1/1415 220/495.08 |
| 2010/0230413 A1 | 9/2010 | Crudgington, Jr. |
| 2011/0168718 A1 | 7/2011 | Tsai et al. |
| 2012/0217247 A1 | 8/2012 | Adkins et al. |
| 2012/0224947 A1 * | 9/2012 | Fitzpatrick et al. .. B65F 1/1415 414/808 |

\* cited by examiner

METHOD OF DISPOSING OF SOILED MATERIALS IN A LINED STORAGE BIN

CROSS-REFERENCE TO RELATED APPLICATIONS

This application is a Continuation of U.S. Utility patent application Ser. No. 13/796,868 filed Mar. 12, 2013, the entire disclosure of which is herein incorporated by reference.

BACKGROUND

1. Field of the Invention

This disclosure relates to systems and methods for disposing of contaminated equipment and supplies, in particular to a lined storage bin which vents air trapped by a liner bag to the environment.

2. Description of the Related Art

Sanitation and sterilization are important to preventing infection and disease in medical practice, particularly in the typical environment where a medical facility and its equipment are used to treat a series of patients. Each treatment may result in the generation of medically contaminated materials ranging from tongue depressors and plastic thermometer covers to surgical towels, gloves, and smocks soiled with bodily fluids from a patient undergoing emergency surgery in an operating room. These materials pose a risk of disease and infection to both the attending staff and future patients treated in the same facility using the same equipment, and both the treatment rooms and equipment are normally sterilized and sanitized before the next patient is treated.

To this end, soiled or potentially contaminated equipment is generally sequestered in disposal bins specially marked as containing contaminated materials. These materials may be items that are intended to be used once on a single patient and then permanently discarded, or equipment that may be sterilized and used again on a subsequent patient. Ideally, after treatment concludes, the treatment room is cleaned and sterilized, and the bag lining the disposal bin is sealed and safely discarded, and a new bag is placed in the disposal bin.

In many contexts, particularly the fast-paced environment of an emergency department or a delicate surgical operation, the doctors, nurses, and staff often do not have time to carefully isolate biologically contaminated materials in conventional storage containers, which are sometimes impractical in this setting for several reasons. The top of such containers must be open-faced so that contaminated materials may be quickly and easily placed into them. However, because the attending personnel are generally moving quickly, they do not have time to carefully place the materials in the bin. Instead, at best, the materials are hastily dropped into the bin, which causes the materials to come into contact with the lip or rim of the container, contaminating it with the very biological material that the container is meant to sequester.

Once the container itself is contaminated, it ceases to serve its purpose unless thoroughly cleaned and sanitized, which costs time and money, assuming it is done at all. If the technicians or other staff responsible for cleaning the operating room neglect to clean the bin, the contaminated container will be used again with the next patient, exposing that patient—and the attending staff—to biological materials from the last patient, thus increasing the risk of infection and disease to both staff and future patients using the operating room.

Ordinarily, this problem would be solved by lining the disposal bin with a flexible liner, such as a sterilized plastic bag. The bag is placed in the bin and the open end of the bag is inverted to cover the rim of the storage bin, similar to a typical residential kitchen trash can. Thus, when biologically contaminated products are deposited in the waste disposal bin, even if some of the biological material comes into contact with the rim, the rim is covered by the plastic bag. When the bag is removed from the bin and sealed, the portion of the bag that was exposed to the contaminated material will be within in the interior of the bag, sequestering the contaminated materials.

However, this solution also presents its own set of problems. First, when a liner bag is placed over the rim, pockets of air generally remain in the bin between the interior surface of the bin and the exterior surface of the bag. When materials are discarded into the bin, the volume of the materials displaces some of the trapped air. Because materials are typically dropped into the bin, this displacement is usually very rapid. Because the containers are typically enclosed except for the central opening, the only major route for the displaced air to flow through is between the exterior of the bag and interior of the bin, ultimately venting into the environment through the opening in the bin by passing between the bag and the rim.

Because the material discarded rapidly displaces the air, the air in turn rapidly ventilates, often dislodging the bag from the rim, which slips partially or completely into the interior of the bin. This then leaves the rim exposed when the next item is discarded, and the doctors and nurses often cannot and should not pause mid-procedure to reattach the bag. The problem is thus worse—not only is the bin exposed to contamination, but the bag that has fallen into the container is also exposed and the exterior of the bag may become contaminated. The staff then must not only safely dispose of the biological material in the container, but also must dispose of the contaminated bag.

This problem might be addressed by fitting a smaller bag to the container so that the fit between the bag and rim is snug, preventing the bag from slipping into the container. However, this only substitutes one problem for another. The tighter fit generally cuts off the primary ventilation route for trapped air. When material is thrown into such a bag, the displaced air is trapped with no escape route, and the total volume available for the air decreases with each item that is thrown into the bin. This places the air under increasing pressure, forcing it to relocate to the area of the bin where it can most expand to equalize pressure with the air in the environment. Because the material in the bag accumulates at the bottom of the bin, the trapped air generally accumulates near the top of the bin, exerting increasing pressure on the exterior of the bag, causing it to collapse and "puff in" from the perception of the user.

As material accumulates in the container, the volume available for the trapped air to occupy decreases and the air pressure on the exterior of the bag increases, further exaggerating the "puffing in" phenomenon. Eventually, the air pressure will either cause the bag to pop or force it off the rim, despite the tighter connection. Either situation reintroduces the problems the bag was meant to solve, as well as the problem of removing a soiled bag. The puffing effect also reduces the amount of available volume within the bag, causing the container to appear "full" even though there is unused storage volume within the bin occupied by the trapped air.

Further, the smaller bag stretched over the rim to achieve a tighter seal is under increased stress, weakening the bag and increasing the risk of a tear, particularly as objects with edges—even blunt edges—are thrown into the container. For example, where the bin is used to hold materials such as a surgical clamp, if a clamp is even gently dropped into the storage bin and impacts the rim, the thinly stretched plastic bag will be caught in the impact between the clamp and the rim. Because the smaller bag is more tightly stretched, the likelihood of the bag tearing in this impact is higher. If the bag tears, the rim of the container is once again exposed to contamination and the bag itself is no longer self-contained when closed. Thus, the entire system does not work, as the container becomes contaminated despite the bag, and the ripped bag is no longer effective at sequestering the contaminated tools or materials stored within it. Similarly, the puffing effect stretches the portion of the bag within the interior of the container, providing an increased surface area to contact discarded materials and giving the bag less flexibility to yield as discarded materials descend into the bin. This in turn also increases the risk of rips or tears in the bag.

This problem might be partially solved by including a shield or grommet which both holds the bag in place around the rim and protects it from being torn by discarded materials impacting the rim. However, this fails to address the problems caused by trapped air and introduces yet further problems. Instead of a contaminated rim that must be resterilized and sanitized before each use, the grommet must be sterilized or replaced. Further, to remove the bag from the container, the grommet first must be removed and set aside. If the contaminated grommet is placed on another surface, that surface may become contaminated and require cleaning and sterilization as well. In the fast-paced environment of a medical services facility, there exists a reasonable likelihood that the staff cleaning the room will not appreciate, or simply overlook, that this surface is now contaminated and must be resterilized, thus reintroducing the problem of exposing the next patient to contaminated materials from a prior patient. Also, by temporarily placing the grommet somewhere else, there is a risk that the grommet will be forgotten in the haste to clean and sterilize the room, thus leaving a contaminated item in the room, and reintroducing the very risk of infection and disease that the bin is meant to reduce.

SUMMARY

Methods and apparatus for maintaining a sanitary disposal and storage bin for consumed medical products using a storage bin with a liner bag and an attached shielding grommet in the shape of a circle flattened on one end which, when soiled, may itself be placed in the liner bag within the container.

There is described herein, among other things, a storage bin comprising: a container having a closed base end and an opposing open top end with an elongated body therebetween, the open top end having a rim circumscribing a generally circular opening providing access to the interior of the enclosed container; a venting grommet attachable to the open top end comprising: an outer wall having opposing top and bottom sides and being generally in the shape of a circular major arc having two terminal ends, the outer wall having a radius larger than the radius of the rim; an inner wall having opposing top and bottom sides and being generally in the shape of a circular major arc the endpoints of which are connected by a chord coplanar with the terminal ends of the outer wall, the inner wall having a radius smaller than the radius of the rim and the inner wall being generally concentric with and circumscribed by the outer wall; a top generally perpendicularly and terminally connected to the top side of the outer wall and the top side of the inner wall; and, wherein when the venting grommet is attached to the open top end of the container, a portion of the rim circumscribes the inner wall and the outer wall circumscribes a portion of the rim; wherein when the venting grommet is rotated about ninety degrees with respect to the generally circular opening, the venting grommet can pass through the generally circular opening.

In an embodiment, the storage bin further comprises: a liner bag having an open end wherein when the liner bag is disposed upon the container such that the open end of the liner bag circumscribes the rim and when the venting grommet is attached to the container, the venting grommet holds the liner bag in place.

In an embodiment of the storage bin, the rim and the outer wall are threaded such that the venting grommet may be screwed unto the rim.

In an embodiment of the storage bin, the storage bin further comprising: the container having an interior surface; and, a liner bag dispensing system comprising: a spindle within the container having opposing top and bottom ends and an elongated body therebetween, the bottom end of the spindle attached to the center of the base end of the container; a support within the interior having opposing top and bottom sides, the top end of the spindle being attached to the support; wherein when a spool of liner bags is placed on the spindle, a liner bag from the spool of liner bags can pass between the support and the interior surface of the container.

In an embodiment, the storage bin further comprising a spool of liner bags disposed on the spindle.

In an embodiment of the storage bin, the length of the spindle is less than half the length of the enclosed container.

In an embodiment of the storage bin, the support is removable from the spindle.

In an embodiment of the storage bin, the height of the inner wall is about the same as the height of the outer wall.

In an embodiment of the storage bin, the radius of the rim is less than the radius of the cylindrical container.

In an embodiment of the storage bin, the venting grommet is made from plastic.

In an embodiment of the storage bin, the distance between the center of the chord and the midpoint of the major circular arc of the outer wall is greater than the radius of the rim and less than the diameter of the rim.

In an embodiment of the storage bin, the distance between the center of the chord and the midpoint of the major circular arc of the outer wall is large enough that the venting grommet cannot pass through the rim into the container unless the rim is deformed into a generally ellipsoid configuration having a major axis greater than the diameter of the rim when the rim is not deformed.

There is also described herein a storage bin comprising: a container defining an interior space and having a rim circumscribing an opening in the container providing access to the interior space; a bag having opposing open and closed ends and being disposed upon the container such that the closed end is within the interior space and the open end circumscribes the rim such that air can flow out of the interior space between the bag and the rim; a venting grommet sized and shaped for attaching to the rim such that when the grommet is attached to the rim the grommet holds the bag in place and leaves a sufficient portion of the bag uncovered that air in the interior space displaced when an object is inserted into the bag can flow out of the interior space between the bag and the rim at the sufficient uncovered portion.

There is also described herein a method for maintaining a sanitized waste disposal bin comprising the steps of: providing a sanitized waste disposal bin comprising: a generally cylindrical container having a hollow interior and a rim circumscribing an opening at one end of the container, a liner bag having opposing closed and open ends, the end disposed on the container such that the open end circumscribes the closed end is within the hollow interior; a venting grommet having a central opening and attached to the one end such that the liner bag is between the rim and the venting grommet; placing refuse in the liner bag through the central opening of the venting grommet attached to the container; removing the venting grommet from the one end; placing the venting grommet in the liner bag within the hollow interior through the rim; removing the liner bag containing the venting grommet from the container, disposing of the liner bag containing the venting grommet; and maintaining a sanitized waste disposal bin.

In an embodiment, the method, further comprising: providing a spool of liner bags within the hollow interior, the spool including a second liner bag having an open end attached to the closed end of the liner bag; providing a second venting grommet; detaching the liner bag from the second liner bag; disposing the second liner bag on the container such that the open end of the second bag circumscribes the rim; and attaching the second venting grommet to the rim such that the second liner bag is between the rim and the second venting grommet.

DESCRIPTION OF THE PREFERRED EMBODIMENTS

The systems, devices, and methods described herein generally include a lined storage bin comprising a container, a venting grommet, and a liner bag. In an embodiment, the systems, devices, and methods may further comprise a bag storage and dispensing system. The venting grommet is generally sized and shaped to provide a ventilation route for trapped air to escape rapidly from the storage container when displaced by the volume of items disposed in the bin. The venting grommet also generally holds the liner bag in place while also permitting a loose enough fit between the liner bag and the rim that sufficient air may rapidly escape through the ventilation route by passing between the liner bag and the rim without dislodging the bag from the rim.

Such systems can be particularly useful for the storage of medical reusables, particularly items that may be used multiple times at different points on the same procedure with one patient, but which need to remain sterile (other than for contact with that one patient) during the procedure. They may then be traditionally resterilized or disposed of. These types of devices generally need a semi-sterile location to be placed during the procedure, semi-sterile in that the location is clean with regards to contact with body fluids from other patients, but not clean with regards to body fluids from this patient. The devices also need to remain easily accessible to the person performing the procedure. As a non-limiting example, a medical device such as a surgical clamp may be in this category. The same clamp may be used at multiple points during a procedure without it needing to be cleaned or resterilized (since all contamination is from this patient). However, the clamp cannot be placed on a non-sterile surface or storage device during the procedure, as then it could not be reused with this patient.

Although the present disclosure is generally in conjunction with storing medically contaminated products, tools, or materials, one of ordinary skill in the art will understand this disclosure to encompass other uses for the systems, devices, and methods described herein. The present disclosure is suitable for use in any setting in which it is desirable that a material or tool be sequestered or isolated. By way of example and not limitation, the present disclosure is suitable for use with materials that are, become, or are exposed to, radioactive compounds or materials. Such embodiments may include additional or modified components, including but not limited to liners designed for use in sequestering radioactive materials.

The devices, systems, and methods described herein generally include a storage container, a venting grommet, and one or more bag liners. The devices, systems, and methods described herein also generally include the disposing of potentially contaminated objects by placing such objects in a liner bag lining the interior of a storage container by inserting the objects through the central opening in a venting grommet attached to the rim of the storage container, and placing the venting grommet itself in the liner bag before removing the liner bag from the storage container.

Figure 1:
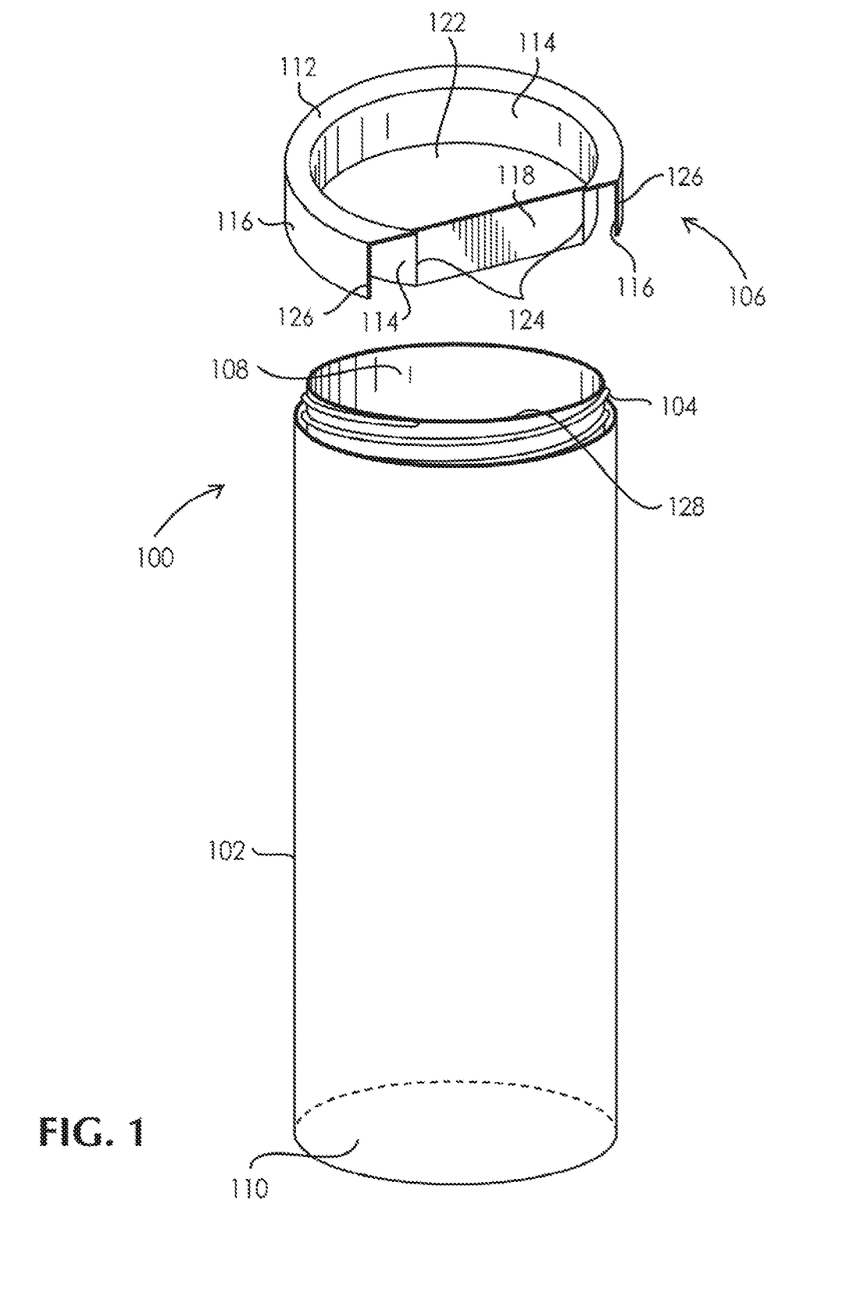
FIG. 1 provides a side elevation view of one embodiment of a lined storage bin and venting grommet.

In the depicted embodiment of FIG. 1, an exploded view of a storage bin 102 and a venting grommet 106 is provided. The depicted storage bin 102 is a generally cylindrical container having a hollow interior and two ends 108, 110, one of which is an open end and the other of which is a generally solid base 110. When the bin 102 is placed for use, the base 110 is normally in contact with the surface on which the bin 102 rests, and the base 110 is generally flat so that the bin 102 stands upright when placed on a flat surface.

In the depicted embodiment, the base 110 is generally sized and shaped similarly to the cross-section of the bin 102 and constructed from the same or similar materials. However, in an embodiment, the base 110 may be sized and shaped differently, such as for fitting into a particular holder designed to accommodate a bin 102, and constructed from or include materials different from those used to construct the bin 102 and/or its subcomponents.

In an embodiment, the base 110 may include a weighting system (not depicted). In such an embodiment, the weighting system moves the center of gravity of the device closer to the surface on which it rests and thus reduces the likelihood of tips, spills, or otherwise dislodging the device from its resting place if jostled or disturbed.

In an alternative embodiment, the base 110 may include a system (not depicted) for increasing the coefficient of the friction between the base 110 and the surface on which it rests, also to reduce spills, tips, and dislodging. Such a system may include, without limitation: rubber feet; a friction pad; a friction coating; texturing, shaping, or sizing to increase friction; adhesive; the use of magnets or magnetism; or other systems.

The depicted bin 102 includes a top end opposite the base 110 which has an opening 108 allowing access to the hollow interior of the bin 102. In the depicted embodiment, the top end is narrower than the base 110, forming a second cylindrical shape having a smaller radius than the bin 102 and attached to the bin 102 at the top end. In the depicted embodiment, the exterior of the storage bin 102 near the opening end 108 is threaded 104 such that a threaded venting grommet 106 may be secured to the storage bin 102 by counter-rotating the bin 102 and/or grommet 106 so that the threads 104 of the bin 102 interlock with the threads in the venting grommet 106.

The cylindrical shape of the storage bin 102, particularly the threaded portion 104, allows a threaded venting grommet 106 to be gently coupled to the storage bin 102. Generally speaking, in an embodiment including a threaded interlocking system, the edges of the threads 104 are not sharp, but rather are smooth and rounded to reduce the likelihood that a bag retained between the threads 104 will be damaged or torn when the venting grommet 106 is attached to the storage bin 102.

Although the body of the storage bin 102, as depicted, is generally cylindrical, other shapes and configurations are possible and specifically contemplated, including without limitation polygonal prisms and ellipsoidal configurations. The diameter of the depicted storage bin 102, as well as the height, may vary from embodiment to embodiment, generally depending upon the type of materials or tools with which a given embodiment is to be used.

By way of example and not limitation, where an embodiment is to be used for a lengthy surgical procedure, a larger bin 102 may be necessary to contain all of the disposed materials and/or tools, whereas a smaller bin 102 may suffice for a shorter or less complex procedure. By contrast, in an embodiment for use in an examining room in a family practice clinic, the bin 102 may primarily hold discarded ear swabs, tongue depressors, plastic slip shields, latex gloves, and the like, and a bin 102 with a shorter height or smaller diameter may be sufficient to accommodate the volume of material accumulated.

Similarly, the diameter of the opening 108 will be sized and shaped to accept the materials and/or tools with which the bin 102 is to be used. In general, the diameter of the opening 108 is large enough to allow the materials to enter the storage bin 102 through the opening 108, but the opening will generally be larger than this to provide a larger target into which users can drop materials, thus improving ease-of-use and reducing the amount of contaminated material that contacts the grommet 106.

In the depicted embodiment of FIG. 1, the top opening 108 is about the same diameter as the body of the storage bin 102. This configuration improves the usage of the interior space of the storage bin 102 because the opening 108 is about the same diameter as the bin 102, and the opening 108 can accommodate the passage of items that are also nearly as large as the diameter of the storage bin 102. This is particularly useful where the items to be inserted are not flexible and cannot be bent or deformed to fit through the opening 108.

The storage bin 102 will generally be made of a material known to one of ordinary skill in the art to be suitable for use in cleaning, sterilization and sanitation procedures for the industry or setting in which a given embodiment is to be used. For example, bins 102 for use in medical facilities will generally be made from smooth plastics, stainless steel, porcelain, or other non-porous solids readily cleanable and sterilizable through use of chemicals and other treatments, including without limitation heat and steam.

The apparatus generally also includes a venting grommet 106, such as the embodiment of a venting grommet depicted in FIGS. 1, 2, 5, 6A, 6B, and 7. In the depicted embodiment of FIG. 2, the venting grommet 106 is sized and shaped for attaching to the open end 108 of the bin 102 such that the grommet 106 generally circumscribes the rim. In the depicted embodiment, the venting grommet 106 is generally in the shape of a flat tire.

Figure 2:
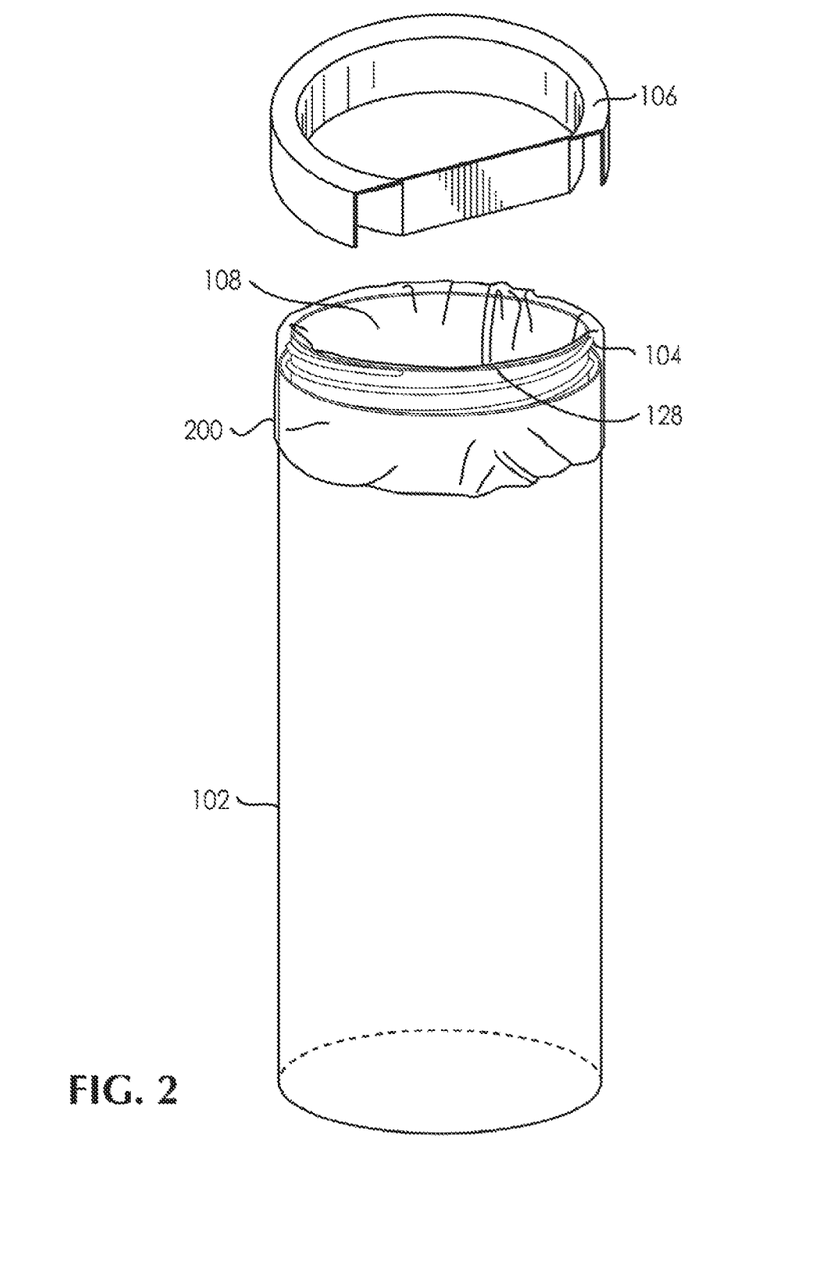
FIG. 2 provides a side elevation view of a lined storage bin including a sanitary disposal bag, and a venting grommet.

The venting grommet 106 serves a number of roles. First, the grommet 106 couples to the bin 102 to hold a liner bag 200 in place. The snugness of the fit between the bag 200 and rim 128 generally is loose enough that air within the bin 102 can, when displaced by objects placed in the bin 102, escape from the bin 102 by passing between the bag 200 and rim 128. This fit is generally loose enough that the force of an item disposed in the bin 102 could dislodge the bag 200 from the rim 128, or the force of the rapid ventilation of the air could itself dislodge the bag 200 from the rim 128. The grommet 106 facilitates the ventilation of air from the bin 102 by, among other things, allowing the bag 200 to be disposed on the rim 128 with a sufficiently loose fit to allow ventilation, while holding the bag 200 in place so that it does not slip into the bin 102 when items are placed in it.

The grommet 106 also provides a rigid shield protecting the rim 128 so that materials dropped or thrown into the bin 102 do not puncture, tear, or otherwise damage the liner bag 200. Further, the grommet 106 provides a filter of appropriately sized items to place in the bin 102—objects which are too large to fit through the central opening 122 in the grommet are large enough to pose a heightened risk of tearing or puncturing the bag 200 when the bag 200 is removed from the container 102.

The "flat tire" shape of the depicted venting grommet 106 is formed from a generally circular major are closed at the end points (124 via a chord (118). The grommet 106 includes a generally circular major arc-shaped inner wall 114 and an outer wall 116, also generally in the shape of a circular major arc. The outer wall 116 generally has a larger radius 612 than the inner wall 114 and is generally concentric with and circumscribes the inner wall 114. These two walls 114, 116 are generally the same thickness and height and are connected at the top end 112, so that the cross-section of the structure is generally that of an inverted square U-shape as depicted in FIG. 6B. This U-shape provides a channel pocket sized and shaped to accommodate, accept, and couple with the rim 128 of the bin 102.

The flat portion 118 of the flat tire shape is generally a flat surface or chord 118 connecting the end points 124 of the interior wall 114. In the depicted embodiments, this flat surface 118 does not extend to the outer wall 116, but rather ends at end points 124 to present the inverted square U-shape cross-section for coupling the grommet 106 to the rim 128. This surface 118 is generally a flat elongated rectangular prism with a height about the same as that of the walls 114, 116. Among other things, this element 118 provides additional rigidity and stability to the grommet 106 so that it maintains its shape.

Figure 7:
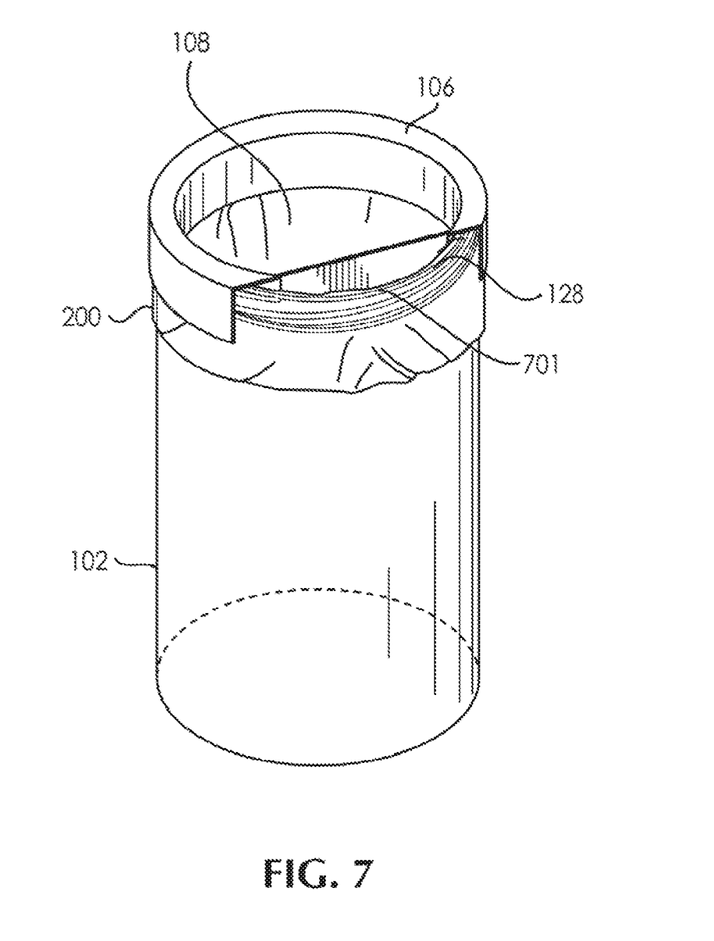
FIG. 7 provides a perspective view of a lined storage bin disposal bag, and a venting grommet, including a sanitary disposal bag, and a venting grommet, with the venting grommet attached to the bin.

As depicted in FIG. 7, the flat portion 118 also results in a portion of the bag 200 disposed upon the rim (128 to be uncovered 701 by the grommet 106. If the fit between the bag 200 and rim 128 is sufficiently loose, air between the bin 102 and the bag 200 can escape from the bin 102 by passing between the bag 200 and the rim 128 at this uncovered portion 701, but there is little risk of the bag 200 becoming dislodged from the rim 128 or otherwise slipping into the bin 102 because the circular portion of the grommet 106 holds the bag 200 in place along the majority of the circumference of the rim 128. Thus, when an object is placed in the bag 200, the volume of the object displaces a volume of air within the bin 102, and that volume of air can vent from the bin 102 without disturbing the bag 200.

Figure 5:
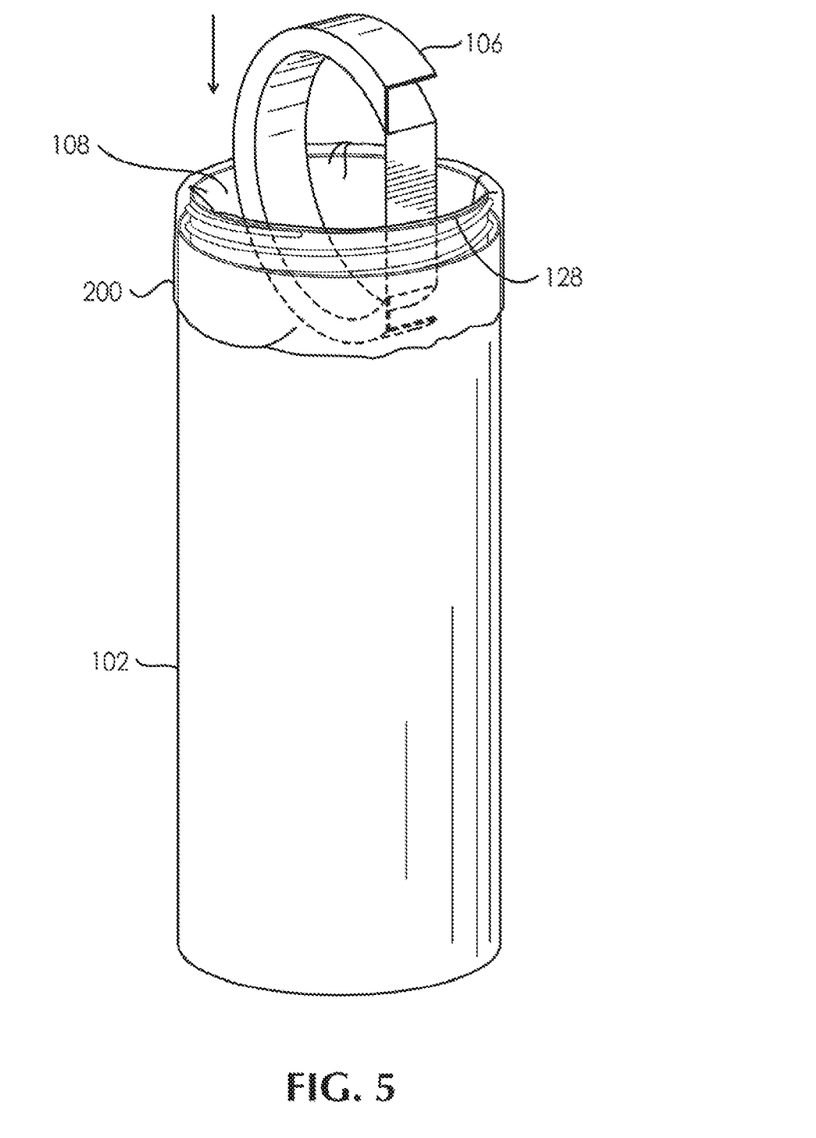
FIG. 5 provides a side elevation view of an embodiment of a venting grommet being inserted into an embodiment of a lined storage bin including a sanitary disposal bag.

The flat chord 118 also allows the grommet 106 to both circumscribe a majority of the rim 128, which in turn circumscribes the opening 108, while also presenting a sufficiently narrow cross-section to, when rotated along a line generally perpendicular to the plane of the chord 118, pass through the opening 108 into the interior of the bin 102, as depicted in FIG. 5. Because the arc-shape leaves a portion 701 of the bag 200 exposed, as depicted in FIG. 7, the chord 118 also provides some protection to the portion 701 of the rim 128 and bag 200 left uncovered by the grommet 106.

In this fashion, the grommet 106 can itself be placed into the bag 200 lining the bin 102. This has the advantage that a soiled or contaminated grommet 106 need not be placed on and contaminate another surface while the bag 200 is being removed from the bin 102, but rather can be removed and placed directly into the bag 200. Also, because the grommet 106 need not be set aside to change the bag 200, cleaning staff are unlikely to leave a soiled grommet 106 in the treatment room, and thus the risk that subsequent treatments or procedures in that room will be exposed to a contaminated grommet 106 is reduced. This also allows a soiled grommet 106 to be placed in the bag 200 while the bag 200 is still disposed upon the rim 128, meaning the soiled grommet 106 is less likely to contaminate the bin 102 itself when the bag 200 is being changed, as the grommet 106 is itself sequestered prior to removing the bag 200.

Figure 6A:
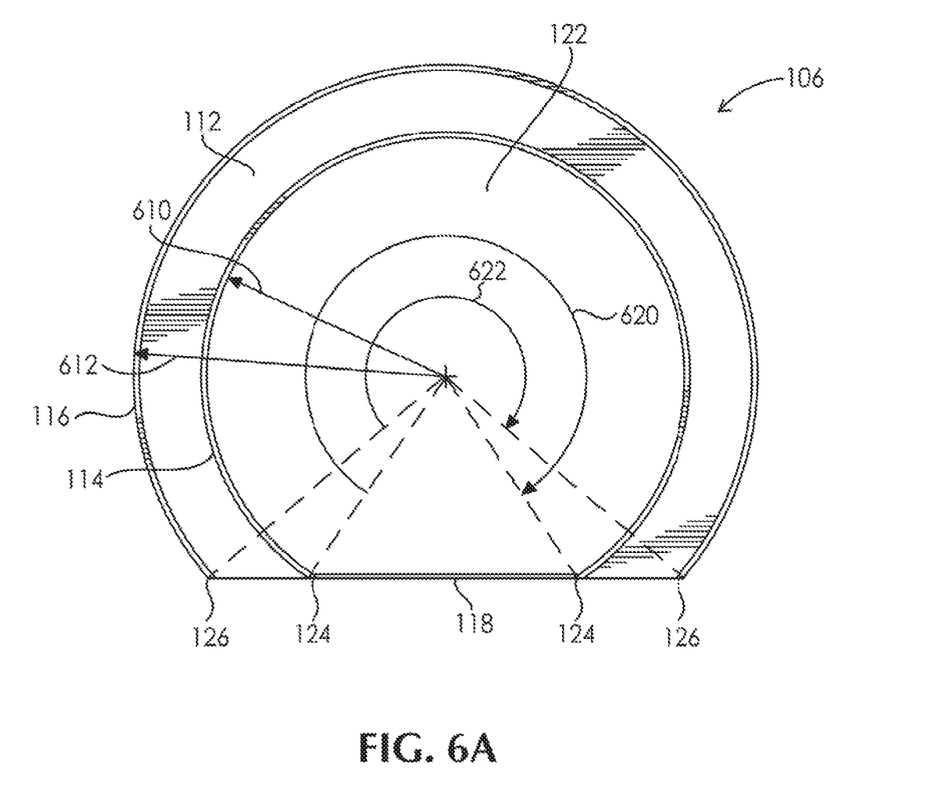
FIG. 6A provides a bottom elevation view of an embodiment of a venting grommet.
Figure 6B:
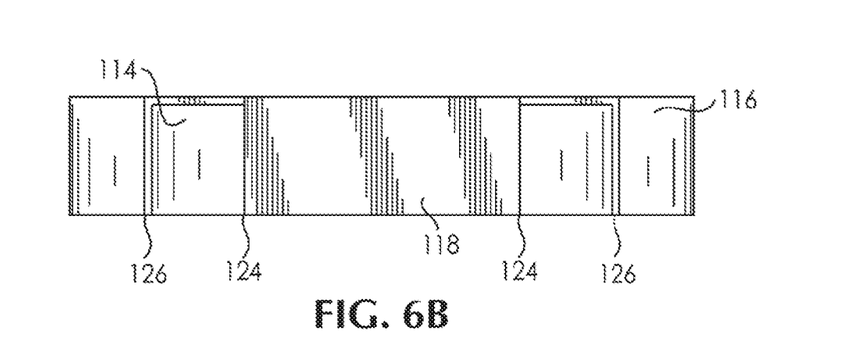
FIG. 6B provides a front elevation view of an embodiment of a venting grommet.

In the depicted embodiment of FIGS. 6A and 6B, some details of the venting grommet 106 are provided. FIG. 6A is a bottom elevation view of a venting grommet 106. As depicted, the interior wall 114 is generally in the shape of a circular arc closed at the end points 124 by a generally flat rectangular prism 118, and generally circumscribed by the exterior wall 116. The exterior wall 116, unlike the interior wall 114, does not include a closing surface between the end points 126, again so that the cross-section provides the square inverted U-shape for coupling the grommet 106 to the rim 128. The angle 620 of the arc of the interior wall 114 is generally slightly larger than the angle 622 of the arc defining the external wall 116. The radius 610 of the arc defining the interior wall 114 is less than that of the radius 612 defining the arc of the exterior wall 116. As depicted, the arc shape is the major arc between end points 124, not the minor arc. In the depicted embodiment, the end points of the walls 114, 116 are generally coplanar with chord 118, producing the "flat tire" shape of the grommet 106 when viewed from the top or bottom.

The grommet 106 includes a central opening 122, as depicted in FIGS. 1 and 6, circumscribed in part by walls 114, 116, through which discarded material is inserted into the storage bin 102 when the device is assembled, as depicted in FIG. 7. In an embodiment, the device is assembled by placing a liner bag 200 within the storage bin 10) and then inverting an open end of the liner bag 200 around the opening 108 in the top of the storage bin 102 and dragging the liner bag down around the outside surface of the rim 128, similar to how garbage bags are attached to garbage cans in ordinary domestic use. The liner bag 200 effectively provides a sanitary shield which prevents the rim 128 of the opening 108 from coming into contact with biological material, thus reducing the need to sanitize or clean the rim 128.

Items placed in the bag 200 may pull the bag 200 into the container 102, causing a portion of the bag 200 situated outside of the container 102 to slip inside the container 102, effectively eliminating the shielding function of the bag 200. As described elsewhere herein, the venting grommet 106 may be attached to the top of the storage container 102, sandwiching the bag 200 between the grommet 106 and the rim 128, to hold the bag 200 in place and reduce the likelihood of such slippage by holding the bag 200 in place.

In an embodiment, the venting grommet 106 may be twisted to engage threads 104 on the rim 128 with threads on the venting grommet 106, establishing a more secure connection between the container 102 and the venting grommet 106. In an alternate embodiment, the venting grommet 106 is sized and shaped to attach to the rim 128 without the use of threads and is held in place through friction between the walls 114,116 and the rim 128. The assembled embodiment depicted in FIG. 7 shows a bag 20) installed in the storage bin 102 and held in place a venting grommet 106 placed over the rim 128 of the bin 102. Contaminated materials may be placed into the storage bin (102) by inserting such materials through the opening 108 and venting grommet 106. The venting grommet 106 will also reduce the likelihood of tearing or ripping of the bag 200 or cracking or damaging the rim 128.

To minimize the amount of the rim 128 which will be exposed 701 when the grommet 106 is attached, the grommet 106 may be sized, shaped, and configured to achieve a long arc-length of walls 114, 116 while still sizing and shaping the grommet 106 to be capable of being inserted through opening 108 when rotated about 90 degrees around an axis generally perpendicular to chord 118, as depicted in FIG. 5. The longer the arc-length of the walls, the smaller the uncovered portion (701) of the bag (200) and/or rim (128), as seen in FIG. 7. However, as the arc-length of the walls 114, 116 approaches 360 degrees, i.e., a circle, the maximum length of the cross section of the grommet 106 when so rotated also increases, eventually becoming larger than the diameter of the opening 108 such that the grommet 106 can no longer pass through the opening 108 even when so rotated. In an embodiment, the arc-lengths of the walls 114, 116 is optimized to maximize the arc-lengths while still configuring the grommet 106 to pass through the opening 108.

In an alternative embodiment, the grommet 106 may be sized, shaped, and configured such that the largest arc-length of walls 114, 116 is too large for the grommet 106 to be capable of being inserted through the opening 108 when rotated with respect to the opening, as depicted in FIG. 5, unless the size and shape of the opening 108 is deformed or otherwise modified into a generally ellipsoid shape having a major axis large enough to accommodate the insertion of the grommet 106. This deforming or modification may be done through any means, including, without limitation, manual compression or squeezing.

In an embodiment, the angle of the arc's defining wall 114 is between 250 and 255 degrees, inclusive. In an embodiment, the angle of the arc's defining wall 114 is between 255 and 260 degrees, inclusive. In an embodiment, the angle of the arc's defining wall 114 is between 260 and 265 degrees, inclusive. In an embodiment, the angle of the arc's defining wall 114 is between 265 and 270 degrees, inclusive. In an embodiment, the angle of the arc's defining wall 114 is between 270 and 275 degrees, inclusive. In an embodiment, the angle of the arc's defining wall 114 is between 275 and 280 degrees, inclusive. In an embodiment, the angle of the arc's defining wall 114 is between 280 and 285 degrees, inclusive. In an embodiment, the angle of the arc's defining wall 114 is between 285 and 290 degrees, inclusive. In an embodiment, the angle of the arc's defining wall 114 is between 290 and 295 degrees, inclusive. In an embodiment, the angle of the arc's defining wall 114 is between 295 and 300 degrees, inclusive. In an embodiment, the angle of the arc's defining wall 114 is between 300 and 305 degrees, inclusive. In an embodiment, the angle of the arc's defining wall 114 is between 305 and 310 degrees, inclusive. In an embodiment, the angle of the arc's defining wall 114 is between 310 and 315 degrees, inclusive. In an embodiment, the angle of the arc's defining wall 114 is between 315 and 320 degrees, inclusive. In an embodiment, the angle of the arc's defining wall 114 is between 320 and 325 degrees, inclusive. In an embodiment, the angle of the arc's defining wall 114 is between 325 and 330 degrees, inclusive. In an embodiment, the angle of the arc's defining wall 114 is between 325 and 330 degrees, inclusive. In an embodiment, the angle of the arc's defining wall 114 is between 330 and 335 degrees, inclusive. In an embodiment, the angle of the arc's defining wall 114 is between 335 and 340 degrees, inclusive.

In an embodiment, the angle of the arc's defining wall 116 is between 250 and 255 degrees, inclusive. In an embodiment, the angle of the arc's defining wall 116 is between 255 and 260 degrees, inclusive. In an embodiment, the angle of the arc's defining wall 116 is between 260 and 265 degrees, inclusive. In an embodiment, the angle of the arcs defining wall 116 is between 265 and 270 degrees, inclusive. In an embodiment, the angle of the arc's defining wall 116 is between 270 and 275 degrees, inclusive. In an embodiment, the angle of the arc's defining wall 116 is between 275 and 280 degrees, inclusive. In an embodiment, the angle of the arc's defining wall 116 is between 280 and 285 degrees, inclusive. In an embodiment, the angle of the arcs defining wall 116 is between 285 and 290 degrees, inclusive. In an embodiment, the angle of the arc's defining wall 116 is between 290 and 295 degrees, inclusive. In an embodiment, the angle of the arc's defining wall 116 is between 295 and 300 degrees, inclusive. In an embodiment, the angle of the arc's defining wall 116 is between 300 and 305 degrees, inclusive. In an embodiment, the angle of the arc's defining wall 116 is between 305 and 310 degrees, inclusive. In an embodiment, the angle of the arc's defining wall 116 is between 310 and 315 degrees, inclusive. In an embodiment, the angle of the arc's defining wall 116 is between 315 and 320 degrees, inclusive. In an embodiment, the angle of the arc's defining wall 116 is between 320 and 325 degrees, inclusive. In an embodiment, the angle of the arc's defining wall 116 is between 325 and 330 degrees, inclusive. In an embodiment, the angle of the arc's defining wall 116 is between 325 and 330 degrees, inclusive. In an embodiment, the angle of the arc's defining wall 116 is between 330 and 335 degrees, inclusive. In an embodiment, the angle of the arc's defining wall 116 is between 335 and 340 degrees, inclusive.

When it is desired to remove the bag, such as when a procedure, examination or treatment is finished and the material in the storage bin 102 should be discarded or sanitized, the venting grommet 106 is likely to have biological or other material on its surface. As materials are discarded through the opening 108, a portion of the discarded material is likely to come in contact with a part of the venting grommet 106, particularly the interior wall 116, leaving a residue of material.

Thus, for the system to remain sanitary, the venting grommet 106 itself may be sanitized or discarded and replaced with a sterile, clean grommet 106. As depicted in the embodiment of FIG. 5, the venting grommet 106 is removed from the rim 128 and inserted into the bag 200 within the storage bin 102 through the opening 108.

Although the outer circumference of the outer wall 116 is greater than that of the rim 128 defining the opening 108, the venting grommet 106 nevertheless can be inserted into the bag 200 through the opening 108 because of the arc shape of the grommet 106. That is, when the grommet 106 is rotated 90 degrees along an axis generally perpendicular to the plane of chord 118, the grommet 106 presents a narrower cross section than when the grommet 106 is oriented for attaching to the rim 128. This allows the grommet 106 to pass through the opening 108 into the bin 102 and/or bag 200. The bag 200 may then be removed from the bin 102 and discarded, or sent for sterilization, where the grommet 106 may be sterilized along with any tools or materials within the bag 200.

Because the rim 128 and the upper portion of the body of the storage bin 102 are protected by the bag 200, the storage bin 102 itself may not generally need to be cleaned, or may require only minimal cleaning and sterilization. The portions of the storage bin 102 that are difficult and time-consuming to clean, such as the threaded 104 rim 128, will not generally require cleaning because they were covered by a bag 200 and the venting grommet 106. This reduces costs and shortens the turnover time for the operating room and its equipment.

Figure 3:
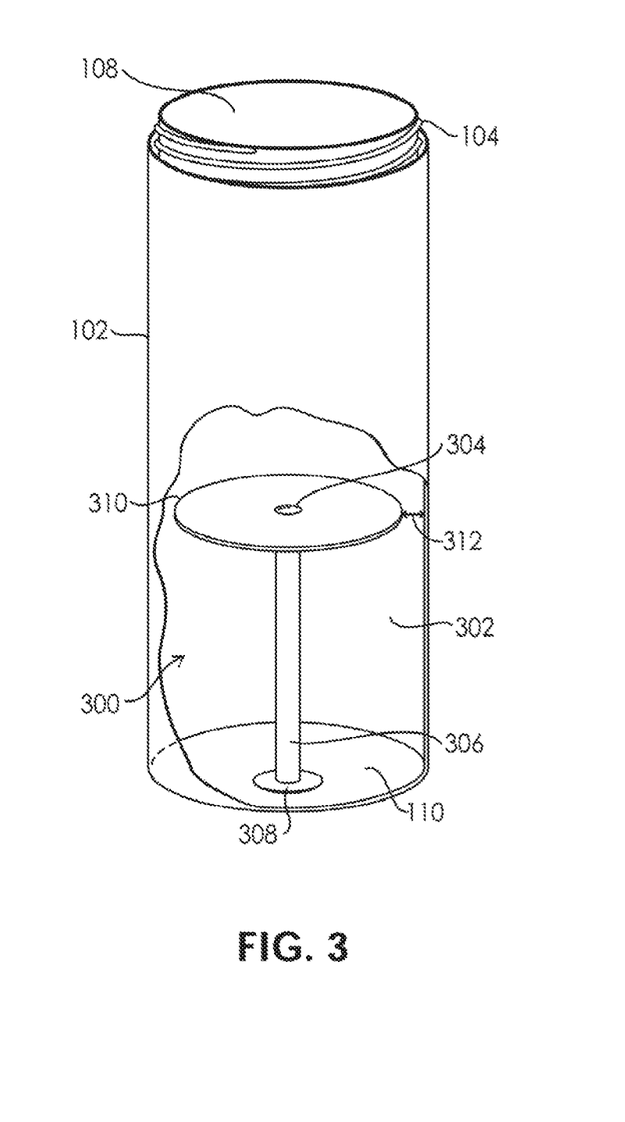
FIG. 3 provides a cross-section side view of an embodiment of a lined storage bin showing an embodiment of an internal bag spooling system.
Figure 4:
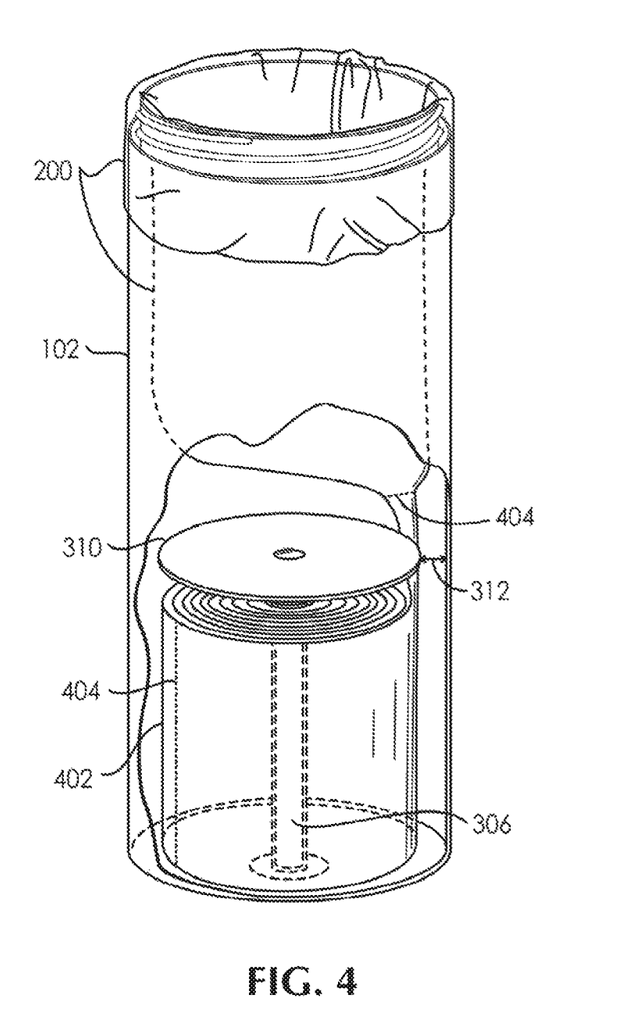
FIG. 4 provides a cross-section side view of an embodiment of a lined storage bin showing an embodiment of an internal bag spooling system, with a spool of bags attached thereto.

In an embodiment, the storage bin 102 is also sized and shaped for housing a bag and/or liner storage and/or dispensing system 300, such as depicted in FIGS. 3-4. In an embodiment, the storage bin 102 further includes a system 300 for storing and dispensing liner bags 200. In the depicted embodiment of FIG. 3, the system 300 includes a spindle 306 attached to a flat, disc-shaped support 310 at one end of the spindle 306 and oriented within the container 102 such that the central axis of the spindle 306 is generally collinear with the central axis of the storage container 102. The bottom of the spindle may be secured to the base 110 of the storage container 102 by a cap 308 which is affixed to the spindle 306 such as by use of adhesive, or hardware. The cap 308 in the depicted embodiment is attached to the exterior of the base 110 and passes through a hole in the base 110 to connect to the spindle 306. The top end of the spindle 306 generally is attached to the support 310 through the use of a second cap 304, which is attached to the spindle 306 in similar fashion to the bottom cap 308.

The support 310 provides a surface on which the bottom of the bag can rest. As materials are placed into the bag, the base 110 would ordinarily provide a resting surface, but in an embodiment, including the depicted bag storage and retrieval system 300, the bottom of the bag 200 does not reach the base. Without a support 110, the bottom of the bag 200 would hang suspended within the bin 102, and as materials are accumulated in the bag 200, they would weigh it down, stretching and stressing the bag and increasing the likelihood of a slip or tear. The support 310 relieves some of this pressure by providing a resting surface for accumulated material in the bag 200.

In the depicted embodiment, the disc is oriented such that the flat surface of the support 310 is generally parallel with the base 110 and opening 108. The diameter of the support 310 is generally sized and shaped such that a gap 312 exists between the outer ridge of the support 310 and the interior of the surface of the storage bin 102 and the gap 312 is wide enough to allow a bag 200 to pass through the gap 312. This arrangement is depicted in FIG. 4. In the embodiment of FIG. 4, a roll of bags 402 is placed on the spindle 306 and unraveled in part, with the unraveled bags being threaded through the gap 312. The topmost bag 200 has an open end which is disposed on the bin 102 as described elsewhere herein.

The spool of bags 402 may include, in an embodiment, a hollow tube at the middle of the spool through which the spindle 306 is inserted, similar to bathroom tissue in a residential building. When the bag 200 is to be discarded, the bag 200 is removed from the bin 102 and sealed, such as by tying, zip tie, or other sealing system, and lifted out of the storage container 102. The roll of bags 402 initially includes a plurality of bags 200 connected to each other from bottom to top along a perforated edge 404. When the bag 200 in use is removed, the perforation 404 is torn, allowing the next bag in the spool 402 to be pulled from the container 102 and opened. By pulling on the top bag 200, the spool 402 will rotate about the spindle 306, allowing the next bag to pass through the gap 312 between the disc 310 and the inner wall of the container 102. In this fashion, each bag 200 in the spool 402 may be used consecutively.

The bin 102 may be used independently or in a storage system and may include further elements not depicted in the Figures. By way of example and not limitation, the bin 102 may include a system for attaching or hanging the bin 102 on equipment, such as a wall, table, gurney, bed, vehicle, chair, or other fixture or device. The bin 102 may also be sized and shaped for attaching to such equipment, such as by having a flat surface to reduce rolling.

In an embodiment, the bin 102 and/or grommet 106 are used in conjunction with a medical procedure, examination, or treatment, and the bin 102 and/or grommet 106 are sterilized and/or sanitized prior to the commencement of the medical procedure, examination, or treatment. In an embodiment, a bag 200 is disposed over the rim 128 and the grommet 106 is attached to the bin 102 before materials are placed in the liner bag 200. Materials are then placed in the bag 200 through the opening 108 of the bin 102 and the opening 122 of the grommet 106. The grommet 106 is then removed from the bin 102 before the bag 200 is removed from the bin, and the grommet 106 is inserted into the bag 200 through the opening 108 in the bin 102 while the bag 200 is still in the bin 102. Then, the bag 200 containing the grommet 106 is removed from the bin 102.

In an embodiment including a bag storage and dispensing system, such as the system depicted in FIGS. 3-4, after the bag 200 containing the grommet 106 is removed from the bin 102, another bag 200 is retrieved from the bag storage and dispensing system and disposed on the rim 128 as described elsewhere herein. A second grommet 106, or the cleaned and/or sterilized first grommet 106, is then attached to the bin 102.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for disposing of soiled materials comprising;
providing a storage bin comprising:
   a container comprising:
      a closed base end and an opposing open top end with an elongated body therebetween, said body having an interior side and an opposing exterior side and said open top end;
      a rim portion at said open top end forming the uppermost edge of said open top end and circumscribing a generally circular opening providing access to the interior of said enclosed container;
      wherein said exterior side comprises a first portion disposed around said rim and having a first radius, and a second portion disposed between said rim and said closed base end and having a second radius larger than said first radius;
      wherein said interior side has a height greater than said second portion;
   a venting grommet attachable to said open top end comprising:
      an outermost wall having opposing top and bottom sides and being generally in the shape of a circular major are having two terminal ends, said outermost wall having a radius larger than the radius of said rim;
      an inner wall having opposing top and bottom sides and being generally in the shape of a circular major arc, the endpoints of which are connected by a chordal wall coplanar with said terminal ends of said outer wall, said inner wall having a radius smaller than the radius of said rim and said inner wall being generally concentric with and circumscribed by said outer wall, and said inner wall and said chordal wall defining the perimeter of a hollow center opening;
      a top generally perpendicularly and terminally connected to said top side of said outer wall and said top side of said inner wall; and,
      wherein said inner wall and said outer wall are about the same height; and
      wherein said inner wall, said outermost wall, and said hollow center opening are generally concentric;
attaching said venting grommet to said open top end of said container so that said outer wall only circumscribes a portion of said rim;
depositing soiled material in said interior of said container by passing said soiled material through said hollow center opening of said venting grommet attached to said open top end;
removing said venting grommet from said open top end;
rotating said venting grommet with respect to said generally circular opening; and
disposing said venting grommet within said interior of said container.

2. The method of claim 1 further comprising:
said storage bin further comprising a liner bag having an open end;

before said attaching step, lining said interior side of said container with said liner bag so that said open end of said liner bag circumscribes said rim;

in said attaching step, said venting grommet holding said liner bag in place; and after said disposing step, closing said open end of liner bag.

3. The method of claim 2, further comprising:

said storage bin further comprising a liner bag dispensing system comprising:

a spindle within said container having opposing top and bottom ends and an elongated body therebetween, said bottom end of said spindle attached to the center of said base end of said container;

a support within said interior having opposing top and bottom sides, said top end of said spindle being attached to said support;

providing a spool of liner bags disposed on said spindle, said liner bag being the first liner bag in said spool of liner bags; and before said lining step, passing said liner bag between said support and said interior side of said container.

\* \* \* \* \*